United States Patent
Chen et al.

(10) Patent No.: US 11,142,534 B2
(45) Date of Patent: Oct. 12, 2021

(54) PROCESS FOR THE PREPARATION OF 3-SUBSTITUTED 5-AMINO-6H-THIAZOLO-[4,5-D]PYRIMIDINE-2,7-DIONE COMPOUNDS

(71) Applicant: Hoffmann-La Roche Inc., Little Falls, NJ (US)

(72) Inventors: Junli Chen, Shanghai (CN); Manuel Konrath, Basel (CH); Roland Meier, Basel (CH); Yan Ren, Shanghai (CN); Xuemei Wang, Shanghai (CN); Jing Xiong, Shanghai (CN); Jianhua Yu, Shanghai (CN)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 16/476,165

(22) PCT Filed: Jan. 4, 2018

(86) PCT No.: PCT/EP2018/050159
§ 371 (c)(1),
(2) Date: Jul. 5, 2019

(87) PCT Pub. No.: WO2018/127525
PCT Pub. Date: Jul. 12, 2018

(65) Prior Publication Data
US 2020/0024287 A1    Jan. 23, 2020

(30) Foreign Application Priority Data

Jan. 6, 2017   (WO) ............... PCT/CN2017/070437
Nov. 21, 2017  (WO) ............... PCT/CN2017/112149

(51) Int. Cl.
*C07D 513/04* (2006.01)

(52) U.S. Cl.
CPC .................................. *C07D 513/04* (2013.01)

(58) Field of Classification Search
CPC .................................................... C07D 513/04
USPC ...................................................... 514/260.1
See application file for complete search history.

(56) References Cited

U.S. PATENT DOCUMENTS

| | | |
|---|---|---|
| 5,041,426 A | 8/1991 | Robins et al. |
| 5,476,659 A | 12/1995 | Goodman et al. |
| 7,560,544 B2 | 7/2009 | Webber et al. |
| 7,709,448 B2 | 4/2010 | Haley |
| 9,441,008 B2 | 9/2016 | Chen et al. |
| 10,040,815 B2 | 8/2018 | Chen et al. |
| 10,618,929 B2 | 4/2020 | Chen et al. |
| 2005/0004144 A1 | 6/2005 | Carson et al. |
| 2016/0194350 A1 | 7/2016 | Chen et al. |

FOREIGN PATENT DOCUMENTS

| | | |
|---|---|---|
| EP | 0343945 A2 | 11/1989 |
| EP | 1072607 A2 | 1/2001 |
| EP | 1973920 B1 | 11/2006 |
| WO | 89/05649 A1 | 6/1989 |
| WO | 98/16184 A2 | 4/1998 |
| WO | 2005/016235 A2 | 2/2005 |
| WO | 2005/025583 A2 | 3/2005 |
| WO | 2006/066080 A1 | 6/2006 |
| WO | 2007/135134 A1 | 11/2007 |
| WO | 2007/150002 A2 | 12/2007 |
| WO | 2008/011406 A2 | 1/2008 |
| WO | 2008/140549 A1 | 11/2008 |
| WO | 2009/026292 A1 | 2/2009 |
| WO | 2016/091698 A1 | 6/2016 |
| WO | 2016/146598 A1 | 9/2016 |
| WO | 2016/180743 A1 | 11/2016 |
| WO | 2017/001307 A1 | 1/2017 |

OTHER PUBLICATIONS

International Preliminary Report on Patentability in PCT/EP2018/050159 dated Jul. 9, 2019.
International Search Report in PCT/EP2018/050159 dated Apr. 24, 2018.
Asselah, T., et al., "Interferon therapy for chronic hepatitis B" Clin Liver Dis 11(4):839-849 (Nov. 1, 2007).
Connolly, D., et al., "New developments in Toll-like receptor targeted therapeutics" Curr Opin Pharmacol 12(4):510-518 (Aug. 1, 2012).
Gane, E., et al., "Safety and pharmacodynamics of oral TLR-7 agonist GS-9620 in patients with chronic hepatitis B" Abstract Ann. Meeting Am. Assoc. Study Liver Dis, Washington, D.C., pp. 661A, Abstract 946 (Nov. 2013).
Hemmi, H., et al., "Small anti-viral compounds activate immune cells via the TLR7 MyD88-dependent signaling pathway" Nat Immunol 3(2): 196-200 (Jan. 22, 2002).

(Continued)

*Primary Examiner* — Kahsay Habte
(74) *Attorney, Agent, or Firm* — Genentech, Inc.; Richard G. A. Bone

(57) ABSTRACT

The present invention relates to a process for synthesizing a compound of formula (I), $R^1$ is H or $C_{1-6}$alkyl; $R^2$ is H or hydroxy; or pharmaceutically acceptable salt or diastereomer thereof, which is useful for prophylaxis and treatment of a viral disease in a patient relating to hepatitis B infection or a disease caused by hepatitis B infection.

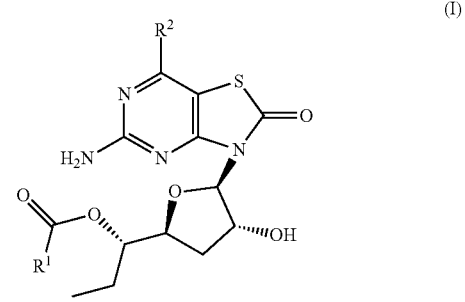

(I)

35 Claims, No Drawings

(56) References Cited

OTHER PUBLICATIONS

Kaisho, T., et al., "Turning NF-kB and IRFs on and off in DC" Trends Immunol 29(7):329-336 (Jul. 1, 2008).
Lee, T., et al., "An expeditious chiral route to analogs of mevinolin and compactin" Tetrahedron Lett 26(41):4995-4996 (1985).
Mereyala, H., et al., "The Role of the C-3 Substituent in the Asymmetric Dihydroxylation of Hexo-5-Enofuranosides" J Carbohydr Chem 19(9):1201-210 (2000).
Roethle, P., et al., "Identification and Optimization of Pteridinone Toll-like Receptor 7 (TLR7) Agonists for the Oral Treatment of Viral Hepatitis" J Med Chem 56(18):7324-7333 (Sep. 26, 2013).

PROCESS FOR THE PREPARATION OF 3-SUBSTITUTED 5-AMINO-6H-THIAZOLO[4,5-D]PYRIMIDINE-2,7-DIONE COMPOUNDS

The present invention relates to a process for the preparation of a compound of formula (Ia),

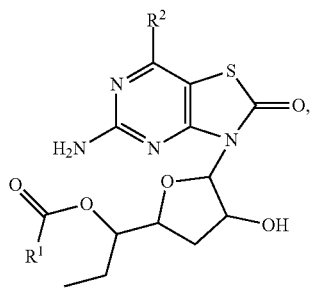

(Ia)

particularly a compound of formula (I),

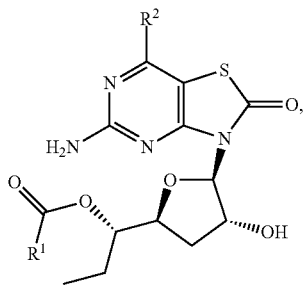

(I)

wherein
$R^1$ is H or $C_{1-6}$alkyl;
$R^2$ is H or hydroxy;
or pharmaceutically acceptable enantiomer or diastereomer thereof, which is useful for prophylaxis and treatment of a viral disease in a patient relating to hepatitis B infection or a disease caused by hepatitis B infection.

BACKGROUND OF THE INVENTION

The synthetic approach of compounds of formula (I) was disclosed in patent WO2016091698, however it is not suitable for commercial process due to the following issues:

(a) the overall yield is very low (0.2-0.5%);
(b) column purification is needed for three of the intermediates, such as: (1S)-1-[(3aR,5S,6aR)-2,2-dimethyl-3a,5,6,6a-tetrahydrofuro[2,3-d][1,3]dioxol-5-yl]propan-1-ol, [(3R,5S)-5-[(1S)-1-acetoxypropyl]-3-hydroxy-tetrahydrofuran-2-yl] acetate and [(2R,3R,5S)-5-[(1S)-1-acetoxypropyl]-2-(5-amino-2-oxo-thiazolo[4,5-d]pyrimidin-3-yl)tetrahydrofuran-3-yl] acetate;
(c) no efficient isolation and purification method for final compound is available, current process must reply on preparative HPLC to obtain qualified final compound due to the poor crystalability of compounds of formula (I).

Based on the issues above, one object of the invention therefore is to find an efficient synthetic approach which can be applied on a technical scale.

Another aspect of the present invention relates to a novel process for the preparation of a compound of the formula (XV) and/or compound (XVa):

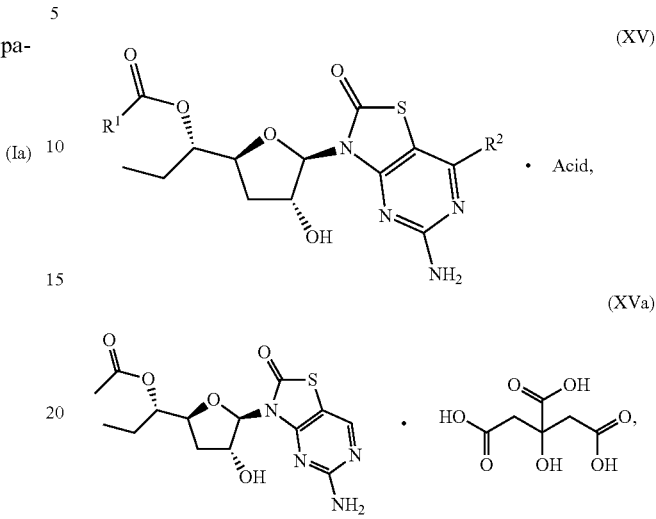

wherein $R^1$ is H or $C_{1-6}$alkyl; $R^2$ is H or hydroxy; or pharmaceutically acceptable salt, enantiomer or diastereomer thereof.

Compound of formula (XV) and compound (XVa) are key intermediates in the synthesis and manufacture of pharmaceutically active compound of formula (I) or compound of formula (Ia) as described herein.

Due to the highly telescoped process toward the preparation of compound of formula (I), direct isolation of compound of formula (I) from reaction mixture gave no direct crystallization as free from. Formation of the compound of formula (XV) proved to be a practice and efficient method for compound purification and isolation.

DETAILED DESCRIPTION OF THE INVENTION

Definitions

As used herein, the term "$C_{1-6}$alkyl" signifies a saturated, linear- or branched chain alkyl group containing 1 to 6, particularly 1 to 5 carbon atoms, for example methyl, ethyl, n-propyl, isopropyl, n-butyl, isobutyl, tert-butyl and the like. Particular "$C_{1-6}$alkyl" group is methyl or ethyl.

The term "halogen" signifies fluorine, chlorine, bromine or iodine, particularly fluorine or chlorine.

The term "enantiomer" denotes two stereoisomers of a compound which are non-superimposable mirror images of one another.

The term "diastereomer" denotes a stereoisomer with two or more centers of chirality and whose molecules are not mirror images of one another.

The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457.

Abbreviation

MeCN Acetonitrile
API active pharmaceutical ingredient
BSA N,O-bis(trimethylsilyl)trifluoroacetamide
DBU 1,8-Diazabicyclo[5.4.0]undec-7-ene
DIPEA N,N-Diisopropylethylamine
eq Equivalent
IPA Isopropanol
IPAc Isopropyl acetate
EtOAc or EA ethyl acetate
MeCy$_2$N N,N-dicyclohexylmethylamine
2-MeTHF 2-Methyltetrahydrofuran
MSA Methanesulfonic acid
MTBE Methyl tert-butyl ether
NMM N-methylmorpholine
TEA Triethylamine
TFA Trifluoroacetic acid
TMPH Tetramethyl piperidine hydride
v/v Volume ratio
wt. % Weight percentage The present invention provides a process for preparing the compounds of formula (X) as outlined in the scheme 1 and compounds of formula (I) as outlined in the scheme 2.

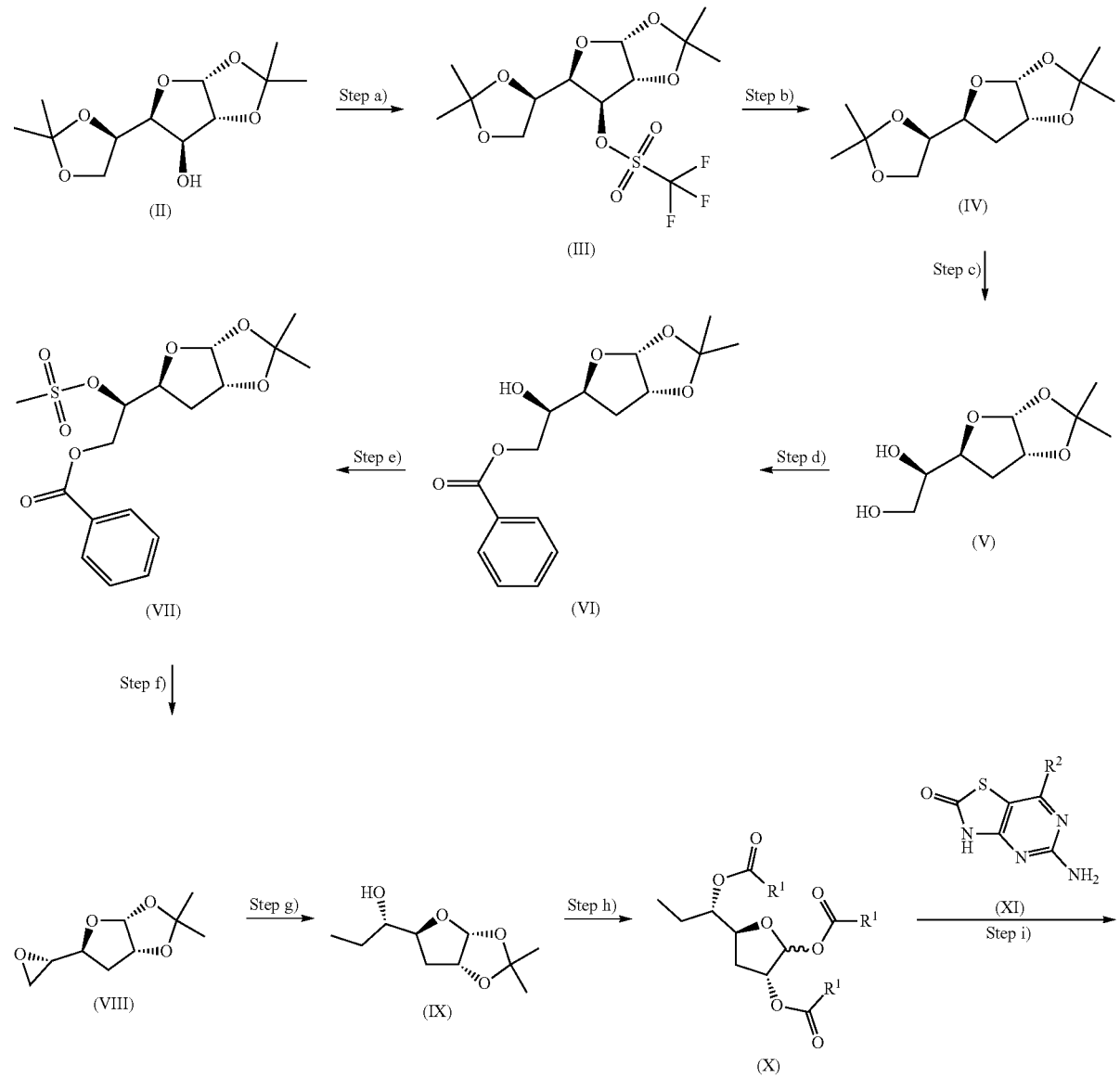

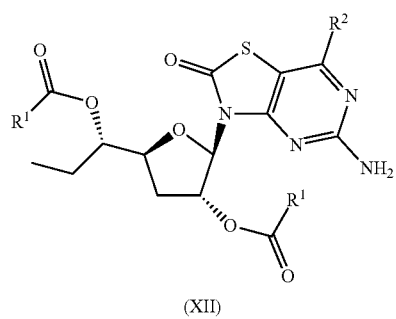
(XII)
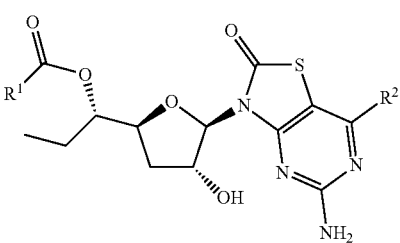
(I)
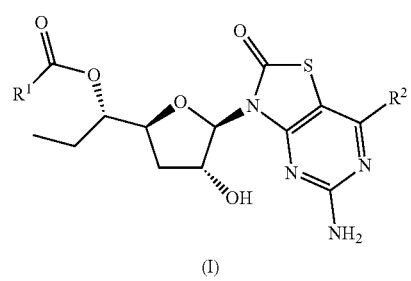
(I)
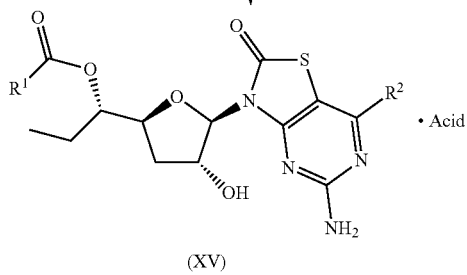
(XV)
wherein R¹ and R² are defined as above.
The synthesis comprises one or more of the following steps:
step a) the formation of compound (III),
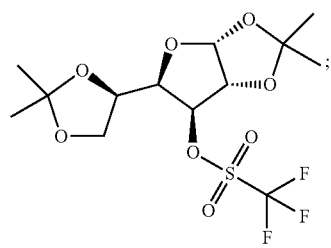
(III)
step b) the formation of compound (IV),
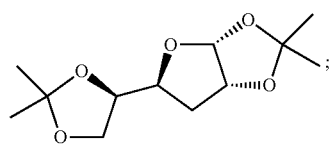
(IV)
step c) the formation of the compound (V),
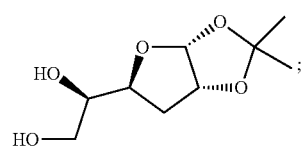
(V)
step d) the formation of compound (VI),
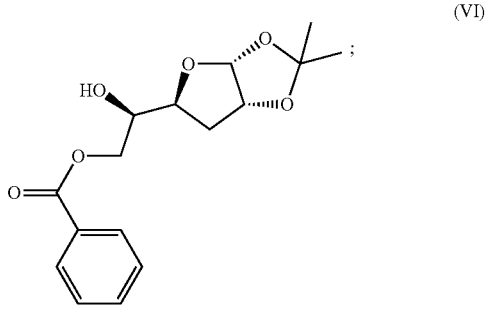 [SMILES: CC1(C)O[C@H]2O[C@H]([C@H](O)COC(=O)c3ccccc3)C[C@H]2O1]
(VI)
step e) the formation of compound (VII),
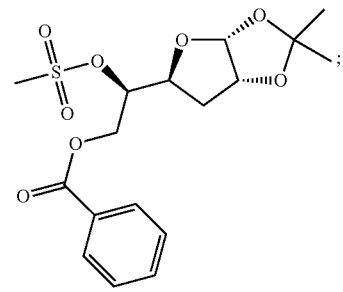
(VII)
step f) the formation of compound (VIII),
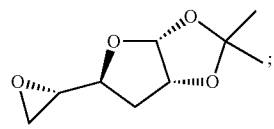
(VIII)

step g) the formation of compound (IX),

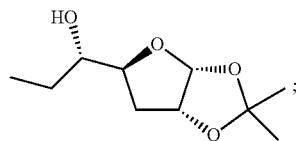

step h) the formation of compound of formula (X),

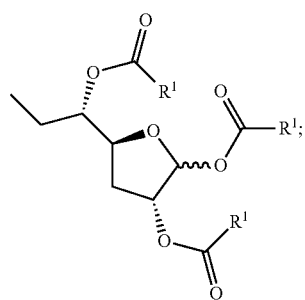

step i) the formation of compound of formula (XII),

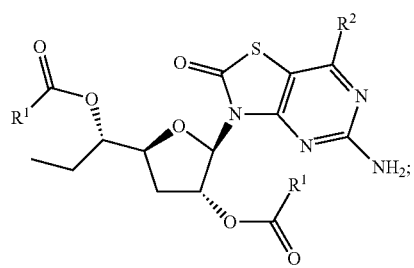

wherein $R^1$ is H or $C_{1-6}$alkyl; $R^2$ is H or hydroxy;

step j) the formation of compound of formula (I) via the hydrolysis of compound of formula (I),

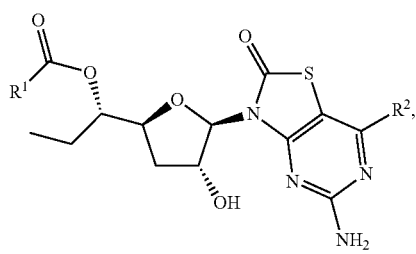

wherein $R^1$ is H or $C_{1-6}$alkyl; $R^2$ is H or hydroxy;

step k) the formation of compound of formula (XV),

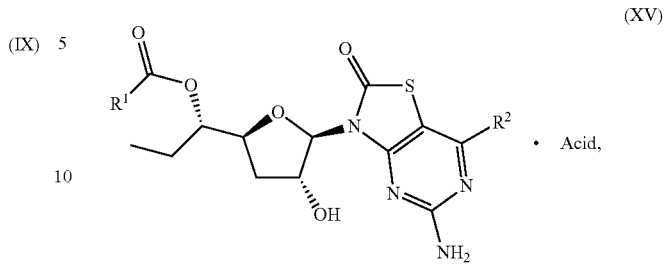

wherein $R^1$ is H or $C_{1-6}$alkyl; $R^2$ is H or hydroxy; the acid is selected from D-glutamic acid, L-mandelic acid, 1-hydroxy-2-naphthoic acid, citric acid, 4-aminosalicylic acid, L-tartaric acid, hippuric acid, malonic acid, glutaric acid, oxalic acid, fumaric acid, succinic acid, 4-aminobenzoic acid, 2,5-dihydroxybenzoic acid, L-malic acid, salicylic acid, maleic acid, (1S,3R)-(−)-camphoric acid, pamoic acid, mucic acid, palmitic acid, oleic acid and lactobionic acid;

step l) the formation of compound of formula (I) via dissociation from compound of formula (XV),

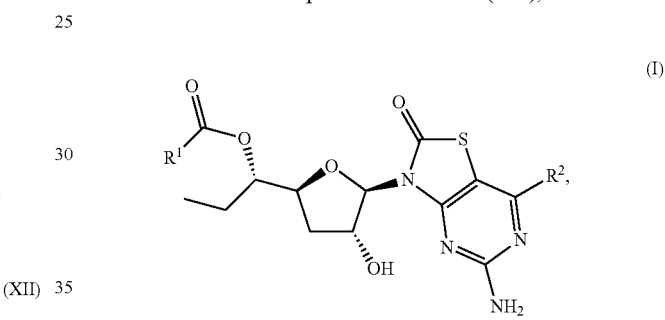

wherein $R^1$ is H or $C_{1-6}$alkyl; $R^2$ is H or hydroxy.

Another embodiment of this invention is that compound of formula (Ia) can also be synthesized in analogy to Scheme 1 with racemic starting material.

A detailed description of present invention of process steps is as following:

Step a) the formation of compound (III).

Compound (III) is synthesized in the presence of a suitable base in a suitable solvent with sulfonating reagent.

The suitable solvent is selected from DCM, CHCl$_3$, benzene, THF, 2-MeTHF, fluorobenzene, pyridine, toluene and xylene; particularly the suitable solvent is toluene.

The suitable base is selected from TEA, DIPEA, TMPH, MeCy$_2$N, NMM, pyridine, K$_2$CO$_3$, Na$_2$CO$_3$ and Cs$_2$CO$_3$; particularly the suitable base is pyridine.

The sulfonating reagent is selected from alkylsulfonic anhydride, alkylsulfonic chloride, arylsulfonic anhydride and arylsulfonic chloride, specifically selected from methanesulfonic anhydride, 4-methylbenzenesulfonic anhydride and Tf$_2$O; particularly the sulfonating reagent is Tf$_2$O.

The reaction is performed at −40° C.-25° C., particularly at 0° C.-10° C.

Step b) the formation of compound (IV).

Compound (IV) is synthesized in a suitable solvent with reducing reagent.

The suitable solvent is selected from benzene, THF, 2-MeTHF, fluorobenzene, xylene and toluene; particularly the solvent is toluene.

The reducing reagent is selected from sodium borohydride, lithium borohydride, sodium cyanoborohydride, triacetoxyborohydride and tetraalkyl ammonium borohydride (such as nBu$_4$NBH$_4$), LAH, Red-Al, hydrogenation with Pd/C and Raney Nickle; particularly the reducing reagent is nBu$_4$NBH$_4$.

The reaction is performed at −20° C.-100° C., particularly at 65° C.-75° C.

In present invention, toluene is used as solvent for step a) in order to telescope step a) and b). The procedure of addition of compound (III) in toluene solution into Bu$_4$NBH$_4$ solution is designed so that it is easy to control the reaction temperature of step b) with higher yield and less by-product.

Step c) the formation of the compound (V).

Compound (V) is synthesized in the presence of a suitable acid and in a suitable solvent.

The suitable solvent is selected from water, a mixture of methanol and water, a mixture of ethanol and water and a mixture of CAN and water; particularly the solvent is a mixture of methanol and water.

The suitable acid is selected from HCl, H$_2$SO$_4$, H$_3$PO$_4$, MSA, TFA, HCOOH, acetic acid and Lewis acid (such as iodine), particularly the acid is H$_2$SO$_4$.

The reaction is performed at −5° C.-50° C., particularly at 5° C.-15° C.

Step d) the formation of compound (VI).

Compound (VI) is synthesized in the presence of a suitable base with a suitable acylating reagent and catalyst in a suitable solvent.

The suitable acylating reagent is selected from alkylacyl anhydride, alkylacyl chloride, arylacyl chloride, specifically selected from isobutyryl chloride, acetyl chloride, methylbenzoyl chloride and benzoyl chloride; particularly the acylating reagent is benzoyl chloride. The amount of acylating reagent is 1.0-2.0 eq., particularly 1.4-1.5 eq.

The suitable catalyst is selected from DMAP, MgCl$_2$ and Bu$_2$SnO; particularly the catalyst is Bu$_2$SnO. The amount of catalyst is 0.001-0.2 eq., particularly 0.05 eq.

In prior art (eg. Carbohydrate Research; 261 (1994); 149-156), pyridine is used as solvent which is highly toxic and difficult to work up. DCM used in current step is more environment benign and operation friendly for scale up.

Catalyst selection is very important in step d) to achieve high conversion as well as high selectivity. If only a base, such as TEA, is presented in this step, the reaction would result in low conversion and poor selectivity (desired: bis-protected byproduct=11:1). Although DMAP as catalyst could improve the conversion (>90%), poor selectivity (desired: bis-protected byproduct=3:2) is still expected. Surprisingly, Bu$_2$SnO served as the catalyst is found to achieve almost complete conversion with significantly increased selectivity (desired: bis-protected byproduct>97:3).

The suitable solvent is selected from DCM, CHCl$_3$, THF, 2-MeTHF, toluene and xylene; particularly the solvent is DCM.

The suitable base is selected from TEA, DIPEA, NMM, pyridine, Na$_2$CO$_3$ and K$_2$CO$_3$; particularly the base is DCM.

The reaction is performed at −20° C.-45° C., particularly at 0° C.-10° C.

Step e) the formation of compound (VII).

Compound (VII) is synthesized in the presence of a suitable sulfonating reagent and a suitable base in a suitable solvent.

The sulfonating reagent is selected from alkylsulfonic anhydride, alkylsulfonic chloride, arylsulfonic anhydride and arylsulfonic chloride, specifically selected from methanesulfonic anhydride, 4-methylbenzenesulfonic anhydride, MsCl and Tf$_2$O; particularly the sulfonating reagent is MsCl.

The suitable solvent is selected from DCM, CHCl$_3$, benzene, THF, 2-MeTHF, fluorobenzene, pyridine and toluene; particularly the solvent is toluene.

The suitable base is selected from TEA, DIPEA, TMPH, MeCy$_2$N, NMM, pyridine, K$_2$CO$_3$, Na$_2$CO$_3$ and Cs$_2$CO$_3$; particularly the suitable base is TEA.

The reaction is performed at −10° C.-25° C., particularly at 0° C.-5° C.

Step f) the formation of compound (VIII).

Compound (VIII) is synthesized in the presence of a suitable base in a suitable solvent.

The suitable base is selected from NaOH, KOH, MeONa, MeOK, t-BuOK and t-BuONa; particularly the base is MeONa.

The suitable solvent is selected from a mixture of DCM and methanol, a mixture of DCM and ethanol and a mixture of THF and methanol; particularly the solvent is a mixture of DCM and methanol.

The reaction is performed at −10° C.-25° C., particularly at 10° C.-15° C.

Step g) the formation of compound (IX).

Compound of formula (IX) is synthesized in the presence of a suitable Grignard reagent with a catalyst.

The Grignard reagent is selected from MeMgCl, MeMgBr and MeMgI; particularly the Grignard reagent is MeMgCl. The Grignard reagent is added at −70° C.-30° C., particularly at −5° C.-0° C.

The suitable catalyst is selected from CuCl, CuI and CuBr, particularly the catalyst is CuCl, with amount of 0.05-0.5 eq., particularly of 0.05 eq.

Step h) the formation of compound of formula (X).

Compound of formula (X) is synthesized in the presence of a suitable acylating reagent with a suitable acid in a suitable solvent.

The suitable acylating reagent is selected from alkylacyl anhydride, alkylacyl chloride, arylacyl chloride, specifically selected from AcCl, Ac$_2$O; particularly the acylating reagent is Ac$_2$O.

The acid is selected from TfOH, MSA, TFA, H$_2$SO$_4$ and a mixture of AcOH and H$_2$SO$_4$; particularly the acid is a mixture of AcOH and H$_2$SO$_4$, which is 1-10 wt. % H$_2$SO$_4$ in AcOH solution, particularly 4 wt. % H$_2$SO$_4$ in AcOH solution.

The solvent is selected from DCM, CHCl$_3$, 2-MeTHF, toluene, IPAc and EtOAc; particularly the solvent is EtOAc.

The reaction is performed at −10° C.-50° C., particularly at 0° C.-40° C.

In prior art (eg. US2016/0194350), this transformation was achieved via a two-step process. First step is the protection of the unprotected secondary alcohol and the second step is a deprotection of the bis-alcohol followed with in-situ protection with acetyl groups. DCM is used as solvent in similar reactions but generates more impurities. EtOAc as the solvent used in step h) of present invention could surprisingly address above issue and results in cleaner reaction and easy work-up.

Step i) the formation of compound of formula (XII).

Compound of formula (XVI) is synthesized in the presence of a suitable acid in a suitable solvent.

The suitable Lewis acid is selected from TMSOTf and TMSI and HI, particularly the acid is TMSOTf, with the amount of 0.05-1.2 eq., particularly 0.05 eq.

The suitable solvent is selected from DCM, CHCl$_3$, benzene, THF, 2-MeTHF, fluorobenzene, xylene, 2,4-dioxane and toluene; particularly the solvent is toluene.

Step j) the formation of compound of formula (I) via the hydrolysis of compound of formula (I).

Compound of formula (I) is synthesized in the presence of a suitable base in a suitable solvent with or without a phase transfer catalyst.

The suitable base is selected from NaOH, KOH, MeONa, MeOK, $K_2CO_3$ and $NH_3 \cdot H_2O$; particularly the base is $K_2CO_3$.

The reaction is performed in the solvent selected from methanol, ethanol, a mixture of methanol and ethanol, a mixture of THF and methanol, and a mixture of 2-MeTHF and methanol; particularly the solvent is a mixture of 2-MeTHF and methanol. The ratio of mixture solvent is selected from 1:1, 1:2, 1:5, 1:10, 10:1, 5:1 and 2:1, particularly the ratio of mixture solvent of 2-MeTHF and methanol is 5:1.

The phase transfer catalyst is selected from PEG-200, PEG-400 and PEG-600; particularly the phase transfer catalyst is PEG-400.

The reaction is performed at 0° C.-45° C., particularly at 25° C.-35° C.

Step k) the formation of compound of formula (XV).

Compound of formula (XV) is synthesized in the presence of a suitable acid in a suitable organic solvent.

The suitable acid is selected from D-glutamic acid, L-mandelic acid, 1-hydroxy-2-naphthoic acid, citric acid, 4-aminosalicylic acid, L-tartaric acid, hippuric acid, malonic acid, glutaric acid, oxalic acid, fumaric acid, succinic acid, 4-aminobenzoic acid, 2,5-dihydroxybenzoic acid, L-malic acid, salicylic acid, maleic acid, (1S,3R)-(−)-camphoric acid, pamoic acid, mucic acid, palmitic acid, oleic acid and lactobionic acid; particularly the acid is selected from 1-hydroxy-2-naphthoic acid, citric acid, 4-aminosalicylic acid, L-tartaric acid, 2,5-dihydroxybenzoic acid; more particularly the acid is citric acid.

The suitable solvent is selected from MeOH, EtOH, n-propanol, IPA, MeCN, acetone, THF, toluene; particularly the solvent is MeCN. In order to improve the purity of compound of formula (XV), an additive can be added to the solvent, wherein the additive is water with volume ratio to solvent ($V_{water}/V_{solvent}$) of 0.005-0.015, particularly of 0.005.

Step k) is critical for the whole process in terms of purity improvement. In present invention, step h), i) and j) are telescoped without solid isolation. Typical purity of crude compound of formula (I) is around 75-90%. Different purification and isolation methods were tried. Direct crystallization of the crude compound of formula (I) was tried under various conditions which either give no precipitation or precipitation with low yield. Silicone-gel column purification to upgrade the crude compound purity to 90-95% followed with crystallization gives acceptable yield but this process is unsuitable for technical scale manufacture. Finally, formation of compound of formula (XV) with carefully selected acid (such as citric acid) and solvent system (such as water and $CH_3CN$, $V_{water}/V_{MeCN}=0.005$) surprisingly gives an efficient and reliable process for technical scale manufacture. The solvent system designed in step k) of present invention gives high yield and good purge effect for impurities.

Step l) the formation of compound of formula (I) via dissociation from compound of formula (XV).

Compound of formula (I) in this step is synthesized via dissociation reaction in the presence of a suitable base in a suitable solvent, followed by a recrystallization procedure.

The suitable base used in dissociation reaction is selected from $Na_2CO_3$, $K_2CO_3$, $NaHCO_3$, $KHCO_3$, NaOH and KOH; particularly the base is $Na_2CO_3$.

The suitable solvent used in dissociation reaction is selected from IPAc, EtOAc, MTBE, toluene, THF, 2-MeTHF; particularly the solvent is IPAc.

The recrystallization is performed in a suitable solvent at 20° C.-70° C., particularly at 40° C.-50° C., for 2-48 hrs, particularly for 19 hrs.

The suitable solvent used in recrystallization procedure is a mixture of water and an organic solvent, wherein the organic solvent is selected from MeOH, EtOH and n-propanol, particularly the organic solvent is EtOH. The suitable weight percentage of organic solvent in water (wt. %) is 0-30 wt. %, particularly 7.8 wt. %.

In another embodiment, the suitable solvent used in recrystallization procedure is a mixture of an polar organic solvent and a non-polar organic solvent; wherein the polar organic solvent is selected from MeOH, EtOH, n-propanol and n-butanol; the non-polar organic solvent is selected from n-heptane and n-hexane; particularly, the solvent used in recrystallization procedure is a mixture of n-propanol and n-heptane. The suitable weight percentage of polar solvent in the solvent mixture is 0-80 wt. %, particularly 60-75 wt. %, more particularly 60 wt. %.

EXAMPLES

The invention will be more fully understood by reference to the following examples. They should not, however, be construed as limiting the scope of the invention.

Example 1

[(3aR,5R,6S,6aR)-5-[(4R)-2,2-dimethyl-1,3-dioxolan-4-yl]-2,2-dimethyl-3a,5,6,6a-tetrahydrofuro[2,3-d][1,3]dioxol-6-yl] trifluoromethanesulfonate (Compound III)

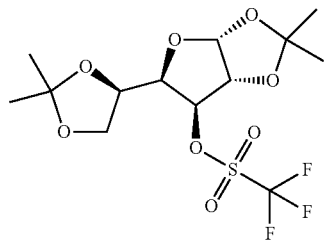

To a 1500 L glass-lined reactor was charged with (3aR,5S,6S,6aR)-5-[(4R)-2,2-dimethyl-1,3-dioxolan-4-yl]-2,2-dimethyl-3a,5,6,6a-tetrahydrofuro[2,3-d][1,3]dioxol-6-ol (compound (II), 60.0 kg, 231 mol), toluene (600 L) and pyridine (36.4 kg, 460 mol) at 5° C.-15° C. After cooled to 0° C.-10° C., the reaction mixture was then charged with $Tf_2O$ (78.0 kg, 276 mol) dropwise at 0° C.-10° C. over 2 hours and stirred at 0° C.-10° C. for another 4 hours. The reaction was then quenched by adding water (180 L) at 0° C.-10° C. slowly. After phase separation, the organic phase was washed with 10% AcOH (240 L, three times), sat. $NaHCO_3$ (240 L, twice) and water (180 L), dried with $Na_2SO_4$ (60 kg) for 4 hours. The solid was removed by vacuum filtration and the wet cake was washed with toluene (30 L). The combined organic phase (solution A) was used for next step without further purification.

Example 2

(3aR,5S,6aR)-5-[(4R)-2,2-dimethyl-1,3-dioxolan-4-yl]-2,2-dimethyl-3a,5,6,6a-tetrahydrofuro[2,3-d][1,3]dioxole (Compound (IV))

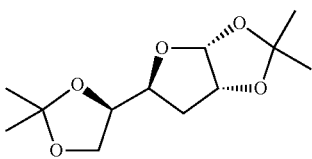

To a 3000 L glass-lined reactor was charged with nBu$_4$NBH$_4$ (119 kg, 462 mol) and toluene (240 L) at 5° C.-15° C. After heated to 65° C.-75° C., to the reaction mixture was then added solution A from previous step dropwise while the reaction temperature was controlled at 65° C.-75° C. After addition, the reaction mixture was stirred at 65° C.-75° C. for 8 hours and then cooled to 0° C.-10° C., quenched by adding water (600 L) slowly while the mixture temperature was controlled at 0° C.-10° C. The resulting mixture was then stirred at 0° C.-10° C. for another hour. After phase separation, the aqueous phase was extracted with 1:1 toluene/n-heptane (600 L, twice). The combined organic phase was washed with 20% NaCl aqueous solution (200 L), then concentrated to form an oil (64.0 kg; 50.4 kg compound (IV) based on assay result) which was used in next step without further purification.

Example 3

(1R)-1-[(3aR,5S,6aR)-2,2-dimethyl-3a,5,6,6a-tetrahydrofuro[2,3-d][1,3]dioxol-5-yl]ethane-1,2-diol (Compound (V))

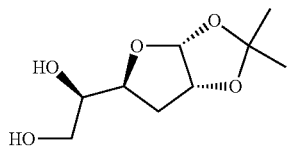

To a 3000 L glass-lined reactor was charged with (3aR,5S,6aR)-5-[(4R)-2,2-dimethyl-1,3-dioxolan-4-yl]-2,2-dimethyl-3a,5,6,6a-tetrahydrofuro[2,3-d][1,3]dioxole (compound (IV), 64.0 kg crude, 50.4 kg by weight assay, 206 mol) and methanol (830 L) at 5° C.-15° C. To the reaction mixture was then added 0.8% aq. H$_2$SO$_4$ solution (224 L) while the reaction temperature was controlled at 5° C.-15° C. After addition, the reaction mixture was heated to 25° C.-30° C. and stirred at this temperature for 16 hours, then cooled to 10° C.-20° C. and quenched by adding 2N NaOH solution (~20 kg) to adjust to pH=7-8. The reaction mixture was concentrated to remove all the volatiles and to the left residue was charged with DCM (900 kg), and the resulting organic solution was dried with Na$_2$SO$_4$ (250 kg) for 8 hours. The solid was removed by vacuum filtration and the solution (34.1 kg compound (V) by weight assay) was used for next step without further purification.

Example 4

[(2R)-2-[(3aR,5S,6aR)-2,2-dimethyl-3a,5,6,6a-tetrahydrofuro[2,3-d][1,3]dioxol-5-yl]-2-hydroxy-ethyl] benzoate (Compound (VI))

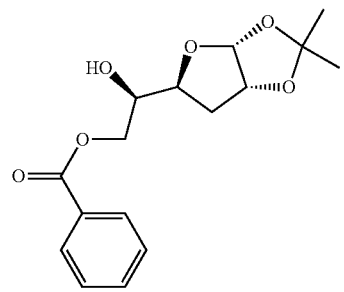 [SMILES: CC1(C)O[C@H]2O[C@H]([C@H](O)COC(=O)c3ccccc3)C[C@H]2O1]

To a 1500 L glass-lined reactor was charged with (1R)-1-[(3aR,5S,6aR)-2,2-dimethyl-3a,5,6,6a-tetrahydrofuro[2,3-d][1,3]dioxol-5-yl]ethane-1,2-diol (compound (V), 63.9 kg by weight assay, 313 mol) in DCM solution, TEA (47.5 kg, 318 mol) and Bu$_2$SnO (3.9 kg, 15.7 mol, 0.05 eq). After cooled to -10° C.-0° C., the reaction mixture was then charged with BzCl (61.8 kg, 440 mol, 1.4 eq) dropwise at -10° C.-0° C., then stirred at 0° C.-10° C. for 1 hour. The reaction was quenched by adding water (50 L) at -10° C.-15° C. slowly, then neutralized with 2 N aq. HCl (~9 L) to adjust to pH=6-7 at -10° C.-15° C. and stirred for 20 minutes. After phase separation, the organic phase was washed with sat. NaHCO$_3$ (100 L) and 20% NaCl (100 L). The resulting organic phase was dried with Na$_2$SO$_4$ (25 kg) for 8 hours. The reaction mixture was filtered through a pad of celite (20 kg) and the organic solution was concentrated under vacuum to remove all the volatile. The resulting crude mixture was suspended in EtOAc (128 L) and n-heptane (512 L) at 15° C.-25° C., then heated to 50° C. and stirred for 2 hours. The reaction mixture was then cooled to 10° C.-20° C. over 2 hours and stir at this temperature for 1 hour. The suspension was separated via centrifuge and the wet cake was dried in vacuum oven (30 mmHg, 50° C.) for 18 hours to afford compound (V) (66.5 kg, 69.0% yield).

Compound (VI): $^1$H NMR (400 MHz, DMSO) δ ppm: 8.05-8.08 (m, 2H), 7.61 (m, 1H), 7.46 (m, 2H), 5.85 (d, J=3.60 Hz, 1H), 4.80 (t, J=4.20 Hz, 1H), 4.47-4.52 (dd, J=11.40, 3.60 Hz, 1H), 4.32-4.39 (m, 2H), 4.21-4.26 (m, 1H), 2.53 (br.s., 1H), 2.11-2.17 (dd, J=13.20, 4.50 Hz, 1H), 1.92-2.02 (m, 1H), 1.53 (s, 3H), 1.34 (s, 3H).

Example 5

[(2R)-2-[(3aR,5S,6aR)-2,2-dimethyl-3a,5,6,6a-tetrahydrofuro[2,3-d][1,3]dioxol-5-yl]-2-hydroxy-ethyl] benzoate (Compound (VII))

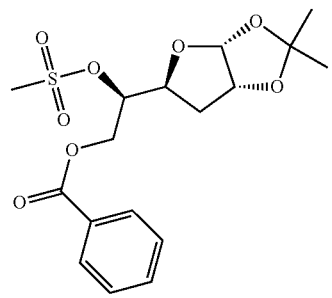

To a 300 L glass-lined reactor was charged with [(2R)-2-[(3aR,5S,6aR)-2,2-dimethyl-3a,5,6,6a-tetrahydrofuro[2,3-d][1,3]dioxol-5-yl]-2-hydroxy-ethyl] benzoate(compound (VI), 25 kg, 81.1 mol), DCM (250 L), DMAP (198 g, 1.62 mol) and TEA (12.3 kg, 82.4 mol). After cooled to 0° C.-5° C., the reaction mixture was then charged with MsCl (11.2 kg, 97.8 mol) at 0° C.-5° C. over 2 hours and stirred at 0° C.-5° C. for 1 hour. The reaction was then quenched by adding water (50 kg) at 0° C.-10° C. The reaction mixture was then charged with 1 N HCl (~12 L) to adjust to pH=5-6 and stir for 20 minutes. After phase separation, the organic phase was washed with sat. NaHCO₃ (50 L) and 20% NaCl (50 L). The resulting organic phase was dried with Na₂SO₄ (20 kg) for 2 hours. The solid was removed by vacuum filtration and the organic solution was used in next step without further purification.

Example 6

(3aR,5S,6aR)-2,2-dimethyl-5-[(2S)-oxiran-2-yl]-3a,5,6,6a-tetrahydrofuro[2,3-d][1,3]dioxole (Compound (VIII))

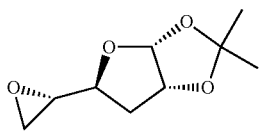

To a 300 L glass-lined reactor was charged with MeOH (50 L) and NaOMe (9.8 kg, 181 mol). After cooled to 5° C.-10° C., the reaction mixture was charged with [(2R)-2-[(3aR,5S,6aR)-2,2-dimethyl-3a,5,6,6a-tetrahydrofuro[2,3-d][1,3]dioxol-5-yl]-2-hydroxy-ethyl] benzoate (compound (VII)) in DCM solution from last step dropwise at 5° C.-10° C. The reaction mixture was stirred at 10° C.-15° C. for 2 hours and then quenched by adding water (100 L). After phase separation, the aqueous phase was extracted with DCM (50 L) and the combined organic phase was washed with 20% NaCl (50 L), and then concentrated under vacuum to remove all the volatile. The residual was then purified by column chromatography to afford crude compound (VIII) (8.4 kg). The crude compound (VIII) was then suspended in n-heptane (5 L). Vacuum filtration and the wet cake was dried under vacuum for 8 hours to afford compound (VIII) (7.76 kg, 51% yield). The reaction time and temperature is critical for this step otherwise over reaction to form the methoxy adduct of the epoxide would take place.

Compound (VIII): ¹H NMR: (300 MHz, CDCl₃) δ ppm: 5.87 (d, J=3.76 Hz, 1H), 4.77 (t, J=4.00 Hz, 1H), 4.20-4.28 (m, 1H), 3.14-3.20 (m, 1H), 2.83-2.88 (m, 1H), 2.63 (dd, J=5.00, 2.80 Hz, 1H), 2.09 (dd, J=12.00, 4.00 Hz, 1H), 1.69-1.79 (m, 1H), 1.52 (s, 3H), 1.34 (s, 3H).

Example 7

(1S)-1-[(3aR,5S,6aR)-2,2-dimethyl-3a,5,6,6a-tetrahydrofuro[2,3-d][1,3]dioxol-5-yl]propan-1-ol (Compound (IX))

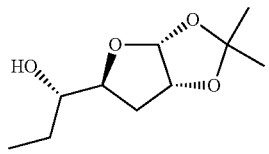

To a 300 L glass-lined reactor was charged with CuCl (520 g, 5.25 mol. 0.05 eq) and THF (71 kg). After cooled to −5° C.-0° C., the reaction mixture was charged with 3N MeMgCl in THF solution (46 kg) dropwise at −5° C.-0° C. and then stirred for 30 minutes at −5° C.-0° C. Then (3aR,5S,6aR)-2,2-dimethyl-5-[(2S)-oxiran-2-yl]-3a,5,6,6a-tetrahydrofuro[2,3-d][1,3]dioxole (compound (VIII), 19.3 kg, 104 mol) in THF (71 kg) solution was added slowly at 0° C.-10° C. The reaction mixture was stirred for 1 hour at 0° C.-10° C., then added into an 1000 L glass-lined reactor containing aq. NH₄Cl (13.5 kg in 121.15 kg water) solution at 0° C.-5° C. over 2 hours, extracted with EtOAc (90 kg) twice. The combined organic phase was washed with 5% NH₃.H₂O aq. solution (7.5 kg), 5% NH₃.H₂O aq. solution (2.5 kg) and 15.6% NaCl aq. solution (30 kg) twice. The organic phase was then concentrated under vacuum to remove all the volatile. To the residue was then charged with n-heptane (5.13 kg), and the resulting mixture was stirred at 50° C. for 30 minutes to form a clear solution, which was slowly cooled to 20° C.-30° C. over 4 hours, and then further cooled to 0° C.-5° C. over 2 hours. The reaction mixture was stirred at 0° C.-5° C. for 30 minutes, then the solid was removed by vacuum filtration and the wet cake was dried in vacuum oven (~30 mmHg, 50° C.) for 6 hours to afford compound (IX) (4.77 kg, 87.8% yield)

Compound (IX): ¹H NMR (400 MHz, CDCl₃) δ ppm: 5.83 (d, J=3.76 Hz, 1H), 4.81-4.73 (m, 1H), 4.26-4.19 (m, 1H), 3.91-3.82 (m, 1H), 2.08-2.02 (m, 1H), 1.93-1.89 (m, 1H), 1.54 (s, 3H), 1.49-1.39 (m, 2H), 1.34 (s, 3H), 1.02 (t, J=7.53 Hz, 3H).

Example 8

[(3R,5S)-5-[(1S)-1-acetoxypropyl]-3-hydroxy-tetrahydrofuran-2-yl] acetate (Compound (Xa))

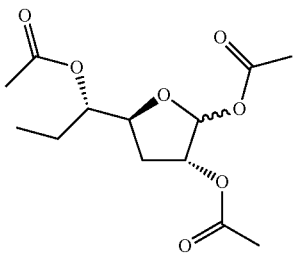

To a 500 L glass-lined reactor was charged with (1S)-1-[(3aR,5S,6aR)-2,2-dimethyl-3a,5,6,6a-tetrahydrofuro[2,3-d][1,3]dioxol-5-yl]propan-1-ol (14.8 kg, 73.2 mol) and EtOAc (72.3 kg). The reaction mixture was stirred at 30° C.-35° C. for 30 minutes then cooled to 0° C.-10° C. over 60 minutes, Then Ac₂O (26.9 kg, 263 mol) and a pre-mixed H₂SO₄ in AcOH solution (0.356 kg H₂SO₄ in 8.90 kg AcOH, or 4 wt. % H₂SO₄ in AcOH) were added at 0° C.-10° C. The reaction mixture was stirred at 0° C.-10° C. for another 30 minutes then heated to 35° C.-40° C. and maintained at this temperature for 2 hours. The reaction mixture was cooled to 0° C.-10° C. and quenched by adding 20% Na₂CO₃ aq. solution (50 L) slowly while the mixture temperature was controlled at 10° C.-20° C. After phase separation, the aqueous phase was extracted by EtOAc (15 L, twice). The combined organic phase was washed with 15.6% NaCl aq. solution (10 L, twice), then concentrated to form an oil (7.0 kg (5.74 kg compound (Xa) by assay)) which was used in next step without further purification.

Example 9

[(2R,3R,5S)-5-[(1S)-1-acetoxypropyl]-2-(5-amino-2-oxo-thiazolo[4,5-d]pyrimidin-3-yl)tetrahydrofuran-3-yl] acetate (Compound (XIIa))

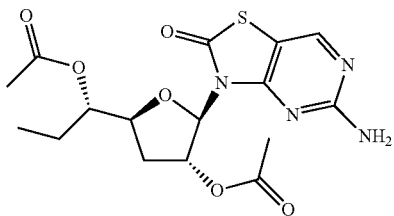 [SMILES: CC[C@H](OC(C)=O)[C@@H]1C[C@@H](OC(C)=O)[C@H](n2c(=O)sc3cnc(N)nc32)O1]

To a 500 L glass-lined reactor was charged with 5-amino-3H-thiazolo[4,5-d]pyrimidin-2-one (8.74 kg, 52.0 mol, 0.94 eq) and toluene (75.7 kg). The reaction mixture was heated to 110° C. and some toluene (37.9 kg) was removed. After cooled to 75° C.-80° C., to the reaction mixture was charged with BSA (25.6 kg, 126 mol, 2.3 eq) over a 40 minutes period. The reaction mixture was then stirred at 75° C.-80° C. for 2 hours, then TMSOTf (1.12 kg, 5.04 mol, 0.05 eq)) was added, followed by addition of [(3R,5S)-5-[(1S)-1-acetoxypropyl]-3-hydroxy-tetrahydrofuran-2-yl] acetate (15.97 kg, 55.4 mol) in toluene (47 kg) solution over a 45 minutes while keeping the temperature at 75° C.-80° C. The reaction mixture was stirred at 75° C.-80° C. for 6.5 hours then cooled to 0° C.-10° C. and quenched by adding water (152.4 kg) at 0° C.-10° C., followed by addition of IPAc (77.4 kg). After phase separation, the aqueous phase was extracted again with IPAc (38.7 kg). The combined organic phase was washed with water (42.6 kg), 15.6% NaCl aq. solution (42.6 kg), and concentrated in vacuum. The residue was dissolved in 2-MeTHF (10.0 kg), then concentrated again, this process was repeated once. The crude product was used in next step without further purification.

Example 10

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate (Compound (Ib))

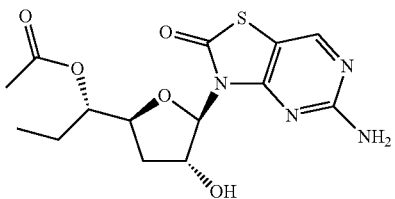 [SMILES: CC[C@H](OC(C)=O)[C@@H]1C[C@@H](O)[C@H](n2c(=O)sc3cnc(N)nc32)O1]

To a 100 L glass jacket reactor was charged with [(1S)-1-[(2S,4R,5R)-5-(5-amino-2-oxo-thiazolo[4,5-d]pyrimidin-3-yl)-4-hydroxy-tetrahydrofuran-2-yl]propyl] acetate (compound (XII), 8.80 kg, 22.2 mol) in 2-MeTHF (6.12 kg) solution from last step, 2-MeTHF (35.66 kg), powder K₂CO₃ (12.47 kg, 90.2 mol), PEG-400 (0.895 kg) and MeOH (6.97 kg). The reaction mixture was stirred at 30° C.-35° C. for 11 hours and the solid was removed through vacuum filtration. The wet cake was washed with IPAc (20.2 kg) and the combined filtrate was washed with water (10 kg), 15.6% aq. NaCl solution (10 kg). The organic phase was concentrated under vacuum to remove all the volatile and the residue was dissolved in MeCN (69.5 kg). The resulting mixture was used in next step without further purification.

Example 11

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate citric acid (Compound (XVa))

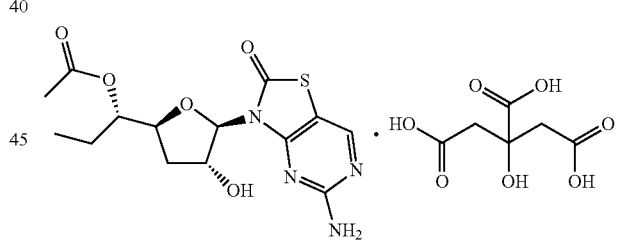

The mixture from last step in Example 10 was heated to 45° C.-52° C. and stirred at 45° C.-52° C. for 30 minutes. To the mixture was then charged with citric acid monohydrate (4.67 kg, 22.2 mol) and water (0.440 kg, $V_{water}/V_{MeCN}=0.005$). The resulting mixture was stirred at 45° C.-52° C. for 4 hours then cooled to 0° C. over 10 hours. The solid was separated via centrifuge and the wet cake was washed with MeCN (1.0 kg), and dried in vacuum oven (30 mmHg, 40° C.) for 32 hours to afford compound (XVa) (9.04 kg, 74.5% yield). The ratio of compound (Ib) and citric acid of compound (XVa) was 1:1 based on the NMR data.

Compound (XVa): ¹H NMR (400 MHz, d₆-DMSO) δ ppm: 8.34 (s, 1H), 6.91 (br. s., 2H), 5.82 (s, 1H), 5.46-5.58 (m, 1H), 4.70-4.82 (m, 2H), 4.14-4.23 (m, 1H), 2.60-2.80 (m, 4H), 2.42-2.48 (m, 1H), 1.98 (s, 3H), 1.78-1.88 (m, 1H), 1.55-1.70 (m, 1H), 1.34-1.49 (m, 1H), 0.82 (t, J=7.40 Hz, 3H). MS obsd. (ESI⁺) [(M+H)⁺]: 355.

Example 12

The Screening of Acid of Compound of Formula (XV)

The formation of Compound of formula (XV) or Compound (XVa) is essential to the scale up and quality control of the Compound of formula (I) or (Ia), which requires a comprehensive design for the choice of acid and solvent system to achieve optimized compound recovery and quality.

Initial Screening:

To a 2 mL Crystal-16 (Technobis Crystal-16) vial was added [(1S)-1-[(2S,4R,5R)-5-(5-amino-2-oxo-thiazolo[4,5-d]pyrimidin-3-yl)-4-hydroxy-tetrahydrofuran-2-yl]propyl] (20 mg, 0.056 mmol), the acid (1.0 eq) and organic solvent (200 μL). The mixture was heated to 50° C. then slowly cooled to 10° C. at a constant cooling rate at 0.2° C./min. The suspension was separated by centrifuge. The result was summarized in table 1.

TABLE 1

Compound (XVa) Screening in MeCN

| Acid | Results of compound of formula (XV) Formation |
|---|---|
| 1-Hydroxy-2-naphthoic acid | Yes |
| Citric acid | Yes |
| 4-Aminosalicyclic acid | Yes |
| L-tartaric acid | Yes |
| 2,5-Dihydroxybenzoic acid | Yes |

Based on the above data, the reaction mixture has larger solubility in acetone. So the formation of compound (XVa) with citric acid in MeCN and 1-Hydroxy-2-naphthoic acid in MeCN were chosen for further scale up with purity analysis.

To a 10 mL Easy-Max test tube reactor (Mettler-Toledo EasyMax) was charged with [(1S)-1-[(2S,4R,5R)-5-(5-amino-2-oxo-thiazolo[4,5-d]pyrimidin-3-yl)-4-hydroxy-tetrahydrofuran-2-yl]propyl] (250 mg, 91.66% purity, 0.80 mmol), the acid (1.0 eq) and MeCN (2.5 mL). The mixture was heated to 50° C. then slowly cooled to −10° C. at a constant cooling rate at 0.2° C./min. If a suspension was formed, the solid was isolated by vacuum filtration and purity was tested by UPLC. The results are summarized in table 3:

TABLE 3

Optimization for compound of formula (XV) formation

| | Result | |
|---|---|---|
| Acid | Suspension formation | UPLC Result |
| Citric acid | Yes | Whole reaction mixture solidified |
| 1-Hydroxy-2-naphthoic acid | Yes | 96.34% |

Based on the data in table 3, the experimental condition of forming compound (XV) with citric acid in MeCN was tested again with increased solvent amount.

To a 250 mL round bottom flask was charged with [(1S)-1-[(2S,4R,5R)-5-(5-amino-2-oxo-thiazolo[4,5-d]pyrimidin-3-yl)-4-hydroxy-tetrahydrofuran-2-yl]propyl] (5.10 g, 16.3 mmol, 91.66% purity), citric acid monohydrate (2.82 g, 14.7 mmol) and MeCN (102 mL). The mixture was stirred at r.t. overnight. The solid was isolated by vacuum filtration and the wet cake was dried in vacuum oven at 40° C. overnight to afford 8.9 g white solid (68.8% yield, 97.31% purity).

Based on the above result, further optimization was performed focusing on further improving product purity. The addition of water as a co-solvent was used to influence the product purity and recovery, another study was carried out to analyze the process impact of different water content.

To a 500 mL round bottom flask was charged with [(1S)-1-[(2S,4R,5R)-5-(5-amino-2-oxo-thiazolo[4,5-d]pyrimidin-3-yl)-4-hydroxy-tetrahydrofuran-2-yl]propyl] (10.0 g, 86.72% purity, 32.0 mmol), citric acid monohydrate (5.83 g, 27.8 mmol), MeCN (200 mL) and water (see Table 4). The mixture was heated to 50° C. then slowly cooled to −10° C. at a constant cooling rate at 0.2° C./min. If a suspension formed, the solid was isolated by vacuum filtration and the wet cake was dried in vacuum oven at 50° C. for 24 hours to afford the product. The result was summarized in table 4.

TABLE 4

Study of Water Effect

| Water (V/V)* | Product purity (UPLC) | Yield |
|---|---|---|
| 0.015 | 98.0% | 64.0% |
| 0.005 | 95.9% | 67.2% |

*volume ratio to MeCN

Since there are two more recrystallization operations in the following steps, higher recovery is more favorable at this step. Based on the above results, compound (XVa) formation by adding 0.9 eq citric acid monohydrate in 20 volume MeCN and 0.1 volume water was selected for scale up.

Example 13

Preparation of [(1S)-1-[(2S,4R,5R)-5-(5-amino-2-oxo-thiazolo[4,5-d]pyrimidin-3-yl)-4-hydroxy-tetrahydrofuran-2-yl]propyl] acetate (Compound (Ib)) from Dissociation of Compound (XVa)

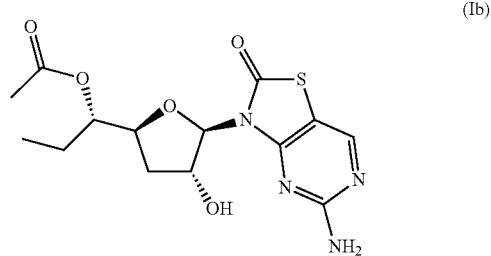 [SMILES: CC[C@H](OC(C)=O)[C@@H]1C[C@@H](O)[C@H](n2c(=O)sc3cnc(N)nc32)O1]

(Ib)

To a 50 L glass jacket reactor was charged with $Na_2CO_3$ (0.819 kg, 7.73 mol) and water (19.8 kg). The mixture was stirred at 20° C.-30° C. for 30 minutes and then IPAc (18.2 kg) and [(1S)-1-[(2S,4R,5R)-5-(5-amino-2-oxo-thiazolo[4,5-d]pyrimidin-3-yl)-4-hydroxy-tetrahydrofuran-2-yl]propyl] acetate citric acid (3.0 kg, 5.49 mol) were added. The reaction mixture was stirred for another 3 hours at 20° C.-30° C. After phase separation, the organic phase was washed with sat. $Na_2CO_3$ aq. solution (20.2 kg), water (20.0 kg), sat. NaCl aq. solution (21.7 kg). Such extraction was repeated twice. The organic solution was concentrated under vacuum to remove the volatile to afford a crude solution (13.04 kg), to which was then added IPAc (6.05 kg). The reaction mixture was then heated to 40° C.-50° C. and stirred for 1 hour, followed by addition of n-heptane (8.05 kg)

slowly and the resulting mixture was stirred at 40° C.-50° C. for another 12 hours. After slowly cooled to 0° C.-10° C. over a 4 hours period and stirred at 0° C.-10° C. for 30 minutes, n-heptane (10.1 kg) was added and the resulting mixture was maintained at 0° C.-10° C. for 2 hours. The suspension was separated by vacuum filtration and the wet cake was washed with n-heptane (6 kg). The wet cake was dried under vacuum oven (30 mmHg, 45° C.) for 19 hours to afford crude compound (Ib) (3.15 kg).

To a 50 L glass jacket reactor was charged with water (35.65 kg), EtOH (3.00 kg, 7.8 wt. % to water) and crude compound (Ib) (3.15 kg). The mixture was heated to 40° C.-50° C. and stirred for 19 hours. Then after cooled to 0° C.-10° C. over 4 hours, a suspension formed and was separated via vacuum filtration, and the wet cake was washed with water (5.00 kg) twice. The wet cake was dried in vacuum oven (30 mmHg, 50° C.) for 24 hours to afford [(1S)-1-[(2S,4R,5R)-5-(5-amino-2-oxo-thiazolo[4,5-d]pyrimidin-3-yl)-4-hydroxy-tetrahydrofuran-2-yl]propyl] acetate (2.76 kg, 99.43% purity, 47.3% yield).

Compound (Ib): $^1$H NMR (400 MHz, d$_6$-DMSO) δ ppm: 8.34 (s, 1H), 6.91 (br. s., 2H), 5.82 (s, 1H), 5.46-5.58 (m, 1H), 4.70-4.82 (m, 2H), 4.14-4.23 (m, 1H), 2.42-2.48 (m, 1H), 1.98 (s, 3H), 1.78-1.88 (m, 1H), 1.55-1.70 (m, 1H), 1.34-1.49 (m, 1H), 0.82 (t, J=7.40 Hz, 3H). MS obsd. (ESI$^+$) [(M+H)$^+$]: 355.

Example 14

Alternative preparation of [(1S)-1-[(2S,4R,5R)-5-(5-amino-2-oxo-thiazolo[4,5-d]pyrimidin-3-yl)-4-hydroxy-tetrahydrofuran-2-yl]propyl] acetate (Compound (Ib)) from Dissociation of Compound (XVa)

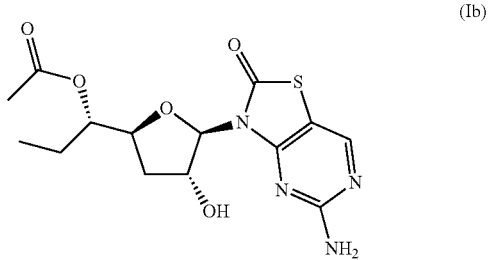 [SMILES: CC[C@H](OC(C)=O)[C@@H]1C[C@@H](O)[C@H](n2c(=O)sc3cnc(N)nc32)O1]

(Ib)

A 1 L glass jacket reactor was charged with sodium carbonate (16.5 g, 155.1 mmol) and water (395 g). The mixture was stirred at 20-30° C. for 30 minutes and then EtOAc (317.3 g) and [(1S)-1-[(2S,4R,5R)-5-(5-amino-2-oxo-thiazolo[4,5-d]pyrimidin-3-yl)-4-hydroxy-tetrahydrofuran-2-yl]propyl] acetate citric acid (50 g, 91.45 mmol) were added. The reaction mixture was stirred for another 2 hours at 35-45° C. After phase separation, the organic phase was washed with sat. NaCl aq. solution (185.5 g). After the second phase separation, a distillation under vacuum was carried out for the organic phase. During this distillation, n-propanol (325 g) was added little by little while liquid level was kept constant. Subsequently, the reaction mixture was concentrated under vacuum until a total mass of 140 g was reached. At atmospheric pressure, the reaction mixture was heated to 60-65° C. and pre-heated (60-65° C.) n-heptane (76.0 g) was added. The clear solution was cooled to 50-55° C., followed by the addition of [(1S)-1-[(2S,4R,5R)-5-(5-amino-2-oxo-thiazolo[4,5-d]pyrimidin-3-yl)-4-hydroxy-tetrahydrofuran-2-yl]propyl] acetate (0.51 g), which served as seed material. The temperature was kept at 50-55° C. for 4 hours. Afterwards, the suspension was cooled to 0-5° C. within 5 hours and held at 0-5° C. for another 12 hours. The suspension was separated by vacuum filtration and the wet cake was washed with a mixture of n-propanol (45.1 g) and n-heptane (30.2 g), then dried in a vacuum oven (25 mbar, 50° C.) for 16 hours to afford compound (Ib) (26.3 g, 99.8% purity, 80.6% yield).

Example 15

[(2R,3R,5S)-5-[(1S)-1-acetoxypropyl]-2-(5-amino-2,7-dioxo-6H-thiazolo[4,5-d]pyrimidin-3-yl)tetrahydrofuran-3-yl] acetate (Compound (XVII))

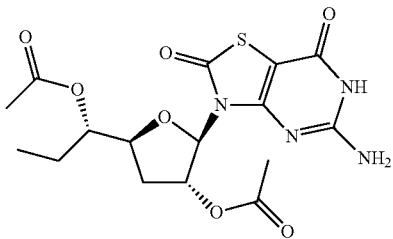 [SMILES: CC[C@H](OC(C)=O)[C@@H]1C[C@@H](OC(C)=O)[C@H](n2c(=O)sc3c(=O)[nH]c(N)nc32)O1]

To a 250 mL round bottom flask was charged with 5-amino-3,6-dihydrothiazolo[4,5-d]pyrimidine-2,7-dione (4.3 g, 22.9 mmol) and toluene (80.5 g). The reaction mixture was heated to 110° C. and some toluene (50 g) was removed. After cooled to 75° C.-80° C., to the mixture was charged with BSA (13.9 g, 68.6 mmol) over a 30 minutes period. The reaction mixture was then stirred at 75° C.-80° C. for 2 hours, then TMSOTf (0.254 g, 1.14 mmol, 0.05 eq) was added, followed by addition of [(3R,5S)-2-acetoxy-5-(1-acetoxypropyl)tetrahydrofuran-3-yl] acetate (7.91 g, 27.4 mmol) in toluene (37.2 g) solution over a 30 minutes period while keeping the temperature at 75° C.-80° C. The mixture was stirred at 75° C.-80° C. for 6.5 hours then cooled to 0° C.-10° C. and quenched by adding water (38 g) at 0° C.-10° C., followed by addition of IPAc (35.0 g). After phase separation, the aqueous phase was extracted with IPAc (35.0 g). The combined organic phases was washed with water (38.0 g), 15.6% NaCl aq. solution (40.5 g), and concentrated in vacuum. The residue was dissolved in 2-MeTHF (20.6 g), and then concentrated again, this process was repeated once. The crude product was used in next step without further purification.

Example 16

[(1S)-1-[(2S,4R,5R)-5-(5-amino-2,7-dioxo-6H-thiazolo[4,5-d]pyrimidin-3-yl)-4-hydroxy-tetrahydrofuran-2-yl]propyl] acetate (Compound (XVIII))

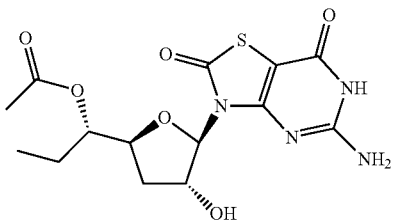 [SMILES: CC[C@H](OC(C)=O)[C@@H]1C[C@@H](O)[C@H](n2c(=O)sc3c(=O)[nH]c(N)nc32)O1]

To a 250 mL round bottom flask was charged with [(1S)-1-[(2S,4R,5R)-5-(5-amino-2,7-dioxo-6H-thiazolo[4,5-d]pyrimidin-3-yl)-4-hydroxy-tetrahydrofuran-2-yl]propyl] acetate (6.0 g, 14.4 mmol) in 2-MeTHF (20.6 g) solution from last step, 2-MeTHF (32.6 g), powder $K_2CO_3$ (2.58 g, 18.7 mmol), PEG-400 (0.06 g) and MeOH (9.5 g). The reaction mixture was stirred at 20° C.-25° C. for 20 hours and the solid was removed through vacuum filtration. The wet cake was washed with IPAc (28.0 g) and the combined filtrate was washed with water (45.0 g), 15.6% aq. NaCl solution (40.0 g). The organic phase was concentrated under vacuum to remove all the volatile and the residue was purified by silica gel column that eluted with DCM/MeOH 30/1 (v/v). The collected fraction was concentrated under vacuum to remove all the solvent to afford compound (XVIII) (2.5 g, 46.3% yield).

The invention claimed is:

1. A process for the preparation of a compound of formula (I),

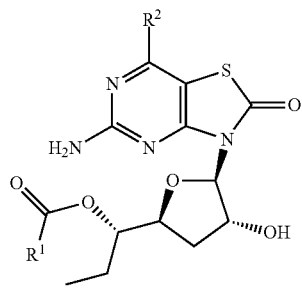

(I)

wherein:
$R^1$ is H or $C_{1-6}$alkyl; and
$R^2$ is H or hydroxy;
or a pharmaceutically acceptable salt, or an enantiomer or diastereomer thereof;

the process comprising one or more of the following steps:

a) forming a compound (III) from a compound of formula (II);

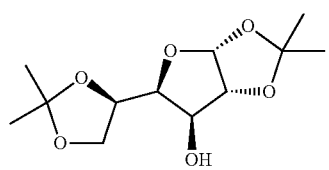

(II)

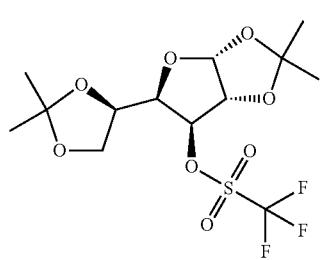

(III)

b) forming a compound (IV) from compound (III);

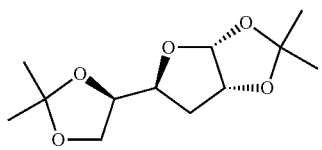

(IV)

c) forming a compound (V) from compound (IV);

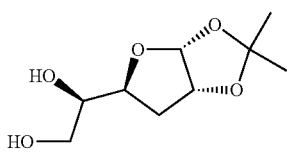

(V)

d) forming a compound (VI) from compound (V);

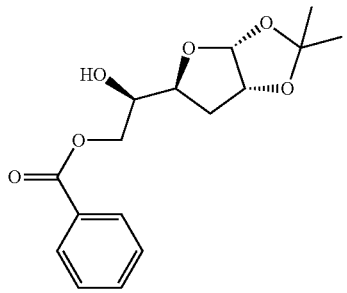

(VI)

e) forming a compound (VII) from compound (VI);

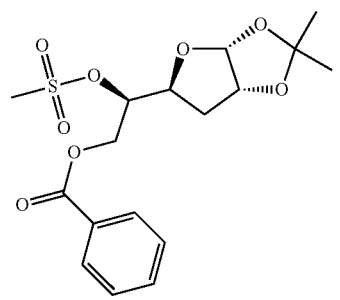

(VII)

f) forming a compound (VIII) from compound (VII);

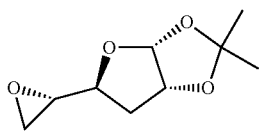

(VIII)

g) forming a compound (IX) from compound (VIII);

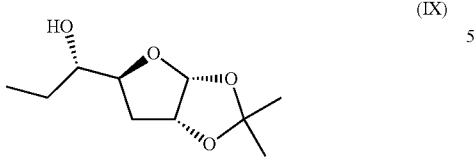
(IX)

h) forming a compound of formula (X) from compound (IX);

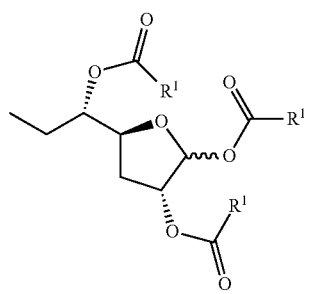
(X)

wherein R¹ is H or $C_{1-6}$alkyl;

i) forming a compound of formula (XII) by reacting compound (X) with a compound of formula (XI);

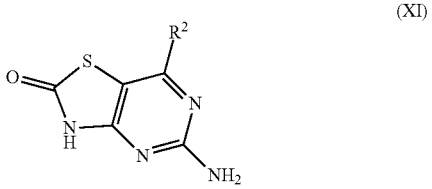
(XI)

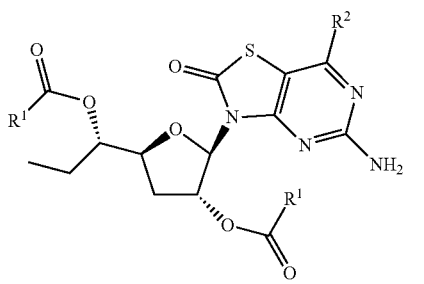
(XII)

wherein R² is H or hydroxy;

j) forming a compound of formula (I) via the hydrolysis of the compound of formula (XII),

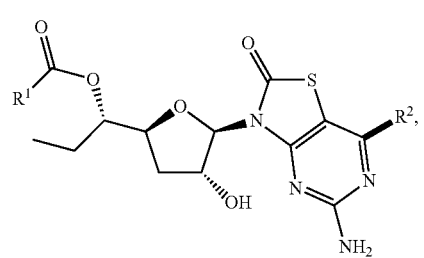
(I)

k) forming a compound of formula (XV) from the compound of formula (I);

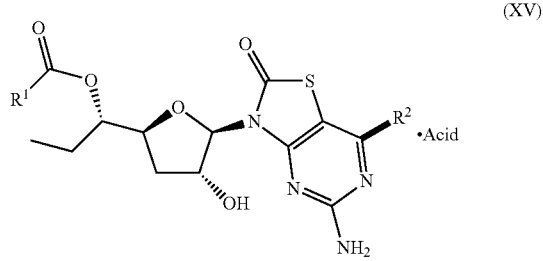
(XV)

wherein Acid is selected from D-glutamic acid, L-mandelic acid, 1-hydroxy-2-naphthoic acid, citric acid, 4-aminosalicylic acid, L-tartaric acid, hippuric acid, malonic acid, glutaric acid, oxalic acid, fumaric acid, succinic acid, 4-amino-benzoic acid, 2,5-dihydroxybenzoic acid, L-malic acid, salicylic acid, maleic acid, (1S,3R)-(−)-camphoric acid, pamoic acid, mucic acid, palmitic acid, oleic acid, and lactobionic acid; and step l) forming a compound of formula (I) via dissociation from the compound of formula (XV).

2. The process according to claim 1 consisting of step a) to step l).

3. The process according to claim 1, wherein R¹ is methyl.

4. The process according to claim 1 for the synthesis of the compound of formula (XV),

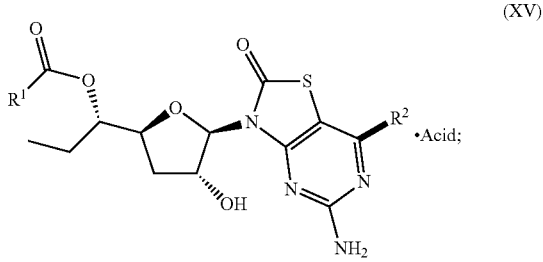
(XV)

wherein:

Acid is selected from D-glutamic acid, L-mandelic acid, 1-hydroxy-2-naphthoic acid, citric acid, 4-aminosalicylic acid, L-tartaric acid, hippuric acid, malonic acid, glutaric acid, oxalic acid, fumaric acid, succinic acid, 4-aminobenzoic acid, 2,5-dihydroxybenzoic acid, L-malic acid, salicylic acid, maleic acid, (1S,3R)-(−)-camphoric acid, pamoic acid, mucic acid, palmitic acid, oleic acid and lactobionic acid;

R¹ is H or $C_{1-6}$alkyl; and

R² is H or hydroxy;

or a pharmaceutically acceptable enantiomer or diastereomer thereof.

5. The process according to claim 4 for the synthesis of compound (XVa),

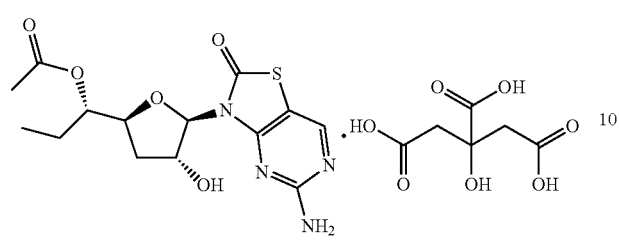
(XVa)

or a pharmaceutically acceptable salt, or an enantiomer or diastereomer thereof.

6. The process according to claim 1, characterized in that the formation of the compound (VI) in step d) is performed in the presence of a base with an acylating reagent and a catalyst, wherein the catalyst is selected from DMAP, $MgCl_2$ and $Bu_2SnO$.

7. The process according to claim 6, wherein the amount of catalyst is 0.001-0.2 eq.

8. The process according to claim 1, characterized in that the formation of the compound of formula (X) in step h) is performed in the presence of an acylating reagent with an acid in a solvent, wherein the solvent is selected from DCM, $CHCl_3$, 2-MeTHF, toluene, IPAc and EtOAc.

9. The process according to claim 1, characterized in that the formation of the compound of formula (XV) in step k) is performed in the presence of an acid in an organic solvent, wherein the acid is selected from: D-glutamic acid, L-mandelic acid, 1-hydroxy-2-naphthoic acid, citric acid, 4-aminosalicylic acid, L-tartaric acid, hippuric acid, malonic acid, glutaric acid, oxalic acid, fumaric acid, succinic acid, 4-aminobenzoic acid, 2,5-dihydroxybenzoic acid, L-malic acid, salicylic acid, maleic acid, (1S,3R)-(−)-camphoric acid, pamoic acid, mucic acid, palmitic acid, oleic acid, and lactobionic acid.

10. The process according to claim 9, wherein the organic solvent is selected from: MeOH, EtOH, n-propanol, IPA, MeCN, acetone, THF, and toluene.

11. The process according to claim 10, wherein the solvent is added with an additive, wherein the additive is water.

12. The process according to claim 11, wherein the volume ratio of water to solvent ($V_{water}/V_{solvent}$) is 0.005-0.015.

13. The process according to claim 11, wherein the solvent is MeCN, and wherein the volume ratio of water to MeCN ($V_{water}/V_{MeCN}$) is 0.005.

14. The process according claim 1, characterized in that the formation of compound of formula (I) via dissociation from compound of formula (XV) in step l) is performed in the presence of a base in a solvent, followed by a recrystallization procedure using a further solvent; wherein the solvent used in the recrystallization procedure is a mixture of water and an organic solvent selected from: MeOH, EtOH, and n-propanol.

15. The process according to claim 14, wherein the weight percentage of organic solvent in water is 0-30 wt. %.

16. The process according claim 1, characterized in that the formation of compound of formula (I) via dissociation from compound of formula (XV) in step l) is performed in the presence of a base in a solvent, followed by a recrystallization procedure using a further solvent;
wherein the solvent used in recrystallization procedure is a mixture of a polar organic solvent and a non-polar organic solvent;
wherein the polar organic solvent is selected from MeOH, EtOH, n-propanol and n-butanol;
and wherein the non-polar organic solvent is selected from n-heptane and n-hexane.

17. The process according to claim 16, wherein the weight percentage of polar solvent in the solvent mixture is 0-80 wt. %.

18. A compound of formula (XV),

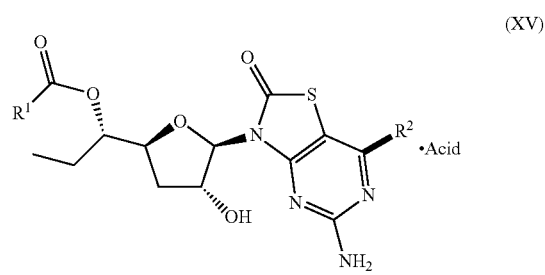
(XV)

wherein:
Acid is selected from D-glutamic acid, L-mandelic acid, 1-hydroxy-2-naphthoic acid, citric acid, 4-aminosalicylic acid, L-tartaric acid, hippuric acid, malonic acid, glutaric acid, oxalic acid, fumaric acid, succinic acid, 4-aminobenzoic acid, 2,5-dihydroxybenzoic acid, L-malic acid, salicylic acid, maleic acid, (1S,3R)-(−)-camphoric acid, pamoic acid, mucic acid, palmitic acid, oleic acid, and lactobionic acid;
$R^1$ is H or $C_{1-6}$alkyl; and
$R^2$ is H or hydroxy;
or a pharmaceutically acceptable salt, or an enantiomer or diastereomer thereof.

19. A compound of formula [(1S)-1-[(2S,4R,5R)-5-(5-amino-2-oxo-thiazolo[4,5-d]pyrimidin-3-yl)-4-hydroxy-tetrahydrofuran-2-yl]propyl] acetate citric acid.

20. The process of claim 4, wherein Acid is selected from the group consisting of: 1-hydroxy-2-naphthoic acid, citric acid, 4-aminosalicylic acid, L-tartaric acid, and 2,5-dihydroxybenzoic acid.

21. The process of claim 4, wherein Acid is citric acid.

22. The process of claim 6, wherein the amount of catalyst is 0.05 eq.

23. The process of claim 6, wherein the catalyst is $Bu_2SnO$.

24. The process of claim 8, wherein the solvent is EtOAc.

25. The process of claim 8, wherein the acid is selected from the group consisting of: 1-hydroxy-2-naphthoic acid, citric acid, 4-aminosalicylic acid, L-tartaric acid, and 2,5-dihydroxybenzoic acid.

26. The process of claim 8, wherein the acid is citric acid.

27. The process of claim 10, wherein the organic solvent is MeCN.

28. The process of claim 14, wherein the volume ratio of water to organic solvent ($V_{water}/V_{solvent}$) is 0.005.

29. The process of claim 15, wherein the weight percentage of organic solvent in water is 7.8 wt. %.

30. The process of claim 14, wherein the organic solvent is EtOH.

31. The process of claim 16, wherein the solvent used in the recrystallization procedure is a mixture of n-propanol and n-heptane.

32. The process of claim 17, wherein the weight percentage of polar solvent in the solvent mixture is 60-75 wt. %.

33. The process of claim 17, wherein the weight percentage of polar solvent in the solvent mixture is 60 wt. %.

34. The compound of claim 18, wherein Acid is selected from 1-hydroxy-2-naphthoic acid, citric acid, 4-aminosalicylic acid, L-tartaric acid, and 2,5-dihydroxybenzoic acid.

35. The compound of claim 18, wherein Acid is citric acid.

* * * * *